Figure 1:
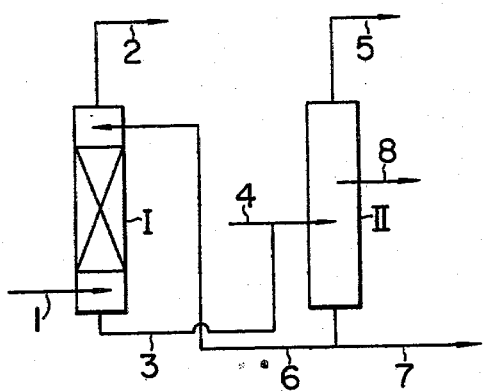

United States Patent [19] [11] 4,228,301
Yoshida et al. [45] Oct. 14, 1980

[54] PROCESS FOR THE PREPARATION OF DIACETOXYBUTENE

[75] Inventors: Yoshinori Yoshida; Hironobu Shinohara, both of Yokohama, Japan

[73] Assignee: Japan Synthetic Rubber Co., Ltd., Tokyo, Japan

[21] Appl. No.: 950,441

[22] Filed: Oct. 11, 1978

[30] Foreign Application Priority Data

Oct. 21, 1977 [JP] Japan .................................. 52-125825
Feb. 8, 1978 [JP] Japan .................................. 53-12348

[51] Int. Cl.$^2$ ............................................. C07C 67/05
[52] U.S. Cl. ....................................... 560/244; 560/246; 203/8; 203/42
[58] Field of Search ............................... 560/244, 246

[56] References Cited

U.S. PATENT DOCUMENTS

| | | | |
|---|---|---|---|
| 3,907,874 | 9/1975 | Harvey | 560/246 |
| 4,044,041 | 8/1977 | Stapp | 560/246 |
| 4,150,239 | 4/1979 | Tanabe | 560/244 |
| 4,152,525 | 5/1979 | Tanabe | 560/244 |

Primary Examiner—Natalie Trousof
Assistant Examiner—Michael Shippen
Attorney, Agent, or Firm—Oblon, Fisher, Spivak, McClelland & Maier

[57] ABSTRACT

In a process for preparing diacetoxybutene by subjecting butadiene, acetic acid and oxygen to reaction, the discharge gas from the reaction system or purification system, containing butadiene and/or acetic acid, is treated by contacting with diacetoxybutene and/or diacetoxybutane (absorbent) to allow butadiene and/or acetic acid to be absorbed by said absorbent. A part of the diacetoxybutene separated in a distillation tower from the reaction product solution containing diacetoxybutene produced by said three-component reaction can be used as said absorbent. In this case, butadiene and/or acetic acid can be recovered from said discharge gas by supplying the absorption solution into said distillation tower. Also usable as said absorbent is diacetoxybutane obtained by hydrogenation of diacetoxybutene. In this case, it is possible to recover butadiene and/or acetic acid by supplying the obtained absorption solution into said distillation tower and further transferring the obtained mixture of diacetoxybutene and diacetoxybutane to the hydrogenation step without separation. In said process for preparing diacetoxybutene, the substantial portion of the discharge gas from the reaction system may be circulated back to the reaction system for reuse, and the remaining discharge gas may be supplied into an absorption tower.

4 Claims, 3 Drawing Figures

PROCESS FOR THE PREPARATION OF DIACETOXYBUTENE

This invention relates to a method for recovering butadiene and/or acetic acid from the butadiene- and/or acetic acid-containing discharge gas from the reaction system or purification system in the process for producing diacetoxybutene by subjecting butadiene, acetic acid and oxygen to reaction in the presence of a nobel metal catalyst such as a palladium catalyst. More particularly, this invention relates to a method for recovering butadiene and/or acetic acid from the above-said discharge gas by allowing such substances to be absorbed by an absorbent, characterized in that at least one material selected from diacetoxybutene, which is a reaction product of the above-said reaction, and diacetoxybutane obtained by the hydrogenation of said diacetoxybutene is used as said absorbent. In a preferred embodiment of this invention, the absorption solution is supplied into a distillation tower used for separation of the reaction product composed mainly of butadiene, acetic acid and diacetoxybutene, whereby the butadiene and acetic acid can easily be separated and recovered.

It is known in the art to produce diacetoxybutene by subjecting butadiene, acetic acid and oxygen to reaction in the presence of a nobel metal catalyst such as a palladium catalyst. A suitable treatment such as hydrogenation or hydrolysis on this diacetoxybutene gives rise to such a substance as diacetoxybutane, butenediol or butanediol. These glycol compounds are widely used as intermediate materials for the preparation of solvents or various kinds of industrially useful compounds. Among these compounds, butanediol is particularly useful as starting material for the preparation of tetrahydrofuran, pyrrolidone, $\gamma$-butyrolactone, etc., as organic solvents or as starting materials for polyesters.

When such useful diacetoxybutene is produced by subjecting butadiene, acetic acid and oxygen to reaction in the presence of a noble metal catalyst such as a palladium catalyst, the discharge gas containing unreacted butadiene and/or acetic acid is released from the reaction system and/or purification system.

Many efforts have been exerted for developing the effective absorbents for butadiene and/or acetic acid because advantageous recovery of butadiene and/or acetic acid is a key factor for successful industrial application of said reaction in the process for the production of diacetoxybutene from said three materials, namely butadiene, acetic acid and oxygen.

For instance, attempts have been made for use of acetic acid as absorbent in recovering butadiene from the discharge gas containing unreacted butadiene. (Japanese Patent Application Kokai (Laid-Open) No. 106,903/75). However, acetic acid is very low in butadiene absorbing efficiency as compared with diacetoxybutene or diacetoxybutane used in this invention, so that it needs to choose the strict absorption conditions for increasing the recovery efficiency. Also, since acetic acid is low in boiling point as compared with the absorbents used in this invention, it is contained in great quantities in the discharge gas released from the top of the absorption tower, which necessitates provision of a separate recovery means for said portion of acetic acid.

An object of this invention, therefore, is to provide a method for recovering said unreacted butadiene and acetic acid in a closed system which allows advantageous industrial practice of the preparation process and which also has no risk of causing the pollution problems.

Other objects and advantages of this invention will become apparent from the following description.

In order to accomplish the above-said objects, the present inventors have carried out their studies assiduously to find that diacetoxybutene, which is a butadiene-acetoxylation product, and diacetoxybutane obtained by the hydrogenation of said diacetoxybutene have an excellent absorbing effect on both butadiene and acetic acid.

According to the present invention, there are provided: (1) a method for treating the butadiene- and/or acetic acid-containing discharge gas from the reaction system or purification system in the production of diacetoxybutene by subjecting butadiene, acetic acid and oxygen to reaction, in which said butadiene- and/or acetic acid-containing discharge gas is contacted with diacetoxybutene and/or diacetoxybutane to allow the butadiene and/or acetic acid to be absorbed thereby; (2) a method for recovering butadiene and/or acetic acid from the butadiene- and/or acetic acid-containing discharge gas from the reaction system in the production of diacetoxybutene by subjecting butadiene, acetic acid and oxygen to reaction, in which the reaction product solution containing diacetoxybutene produced by said reaction is supplied into a distillation tower to separate diacetoxybutene to use a part thereof as absorbent, then the butadiene- and/or acetic acid-containing discharge gas from the reaction system is contacted with said absorbent to allow the butadiene and/or acetic acid to be absorbed by said absorbent, and then this absorption solution is supplied into said distillation tower; (3) a method for treating the butadiene- and/or acetic acid-containing discharge gas for recovering therefrom butadiene and/or acetic acid in the production of diacetoxybutene by subjecting butadiene, acetic acid and oxygen to reaction, in which the butadiene- and/or acetic acid-containing discharge gas from the reaction system is contacted with the diacetoxybutane obtained by the hydrogenation of diacetoxybutene to allow the butadiene and acetic acid to be absorbed by said diacetoxybutane, then this absorption solution is supplied into the distillation tower used for the separation of the reaction product solution containing diacetoxybutene, and the thus obtained mixture of diacetoxybutene and diacetoxybutane is immediately sent to the hydrogenation step without separation.

The discharge gas from the acetoxylation step in the method of this invention usually contains an inert gas such as $N_2$ and $CO_2$ as well as the reactants, namely butadiene, acetic acid and oxygen and a part of $H_2O$ which is a reaction product. The composition of the discharge gas may vary depending on the reaction conditions or reaction product cooling conditions, but it is imperative to use care so that the composition does not become an explosive one.

The gas-liquid equilibrium constant of butadiene in case of using the absorbents composed of diacetoxybutene and diacetoxybutane according to this invention and in case of using acetic acid and light oil as absorbent was measured under the conditions of 65° C. and 3 kg/cm² abs. by using an Othmer type gas-liquid equilibrium meter. The results are shown in Table 1.

TABLE 1

| Absorbent | Gas-liquid equilibrium constant Butadiene |
|---|---|
| Diacetoxybutene | 2.45 |
| Diacetoxybutane | 2.21 |
| Acetic acid | 7.10 |
| Light oil | 2.60 |

The results in the above table dictate that butadiene is absorbed more efficiently by diacetoxybutene and diacetoxybutane than by acetic acid which is a known absorbent. It is also noted that both diacetoxybutene and diacetoxybutane have higher absorbing efficiency than light oil which is popularly used as absorbent in industry, thus indicating excellency of diacetoxybutene and diacetoxybutane as butadiene absorbent. In the method of this invention, this diacetoxybutene and/or diacetoxybutane is contacted with the discharge gas of the abovesaid composition to allow the butadiene and acetic acid in said discharge gas to be absorbed by said diacetoxybutene or diacetoxybutane. The lower the gas absorption temperature, the better, but usually such absorption is performed at a temperature of from 20° to 80° C. As for the pressure used in such absorbing operation, the lowest usable level is determined according to the amount of butadiene and/or acetic acid to be absorbed and the amount of usable diacetoxybutene or diacetoxybutane. From the viewpoint of absorbing efficiency, a pressure as high as possible is recommended, but generally there is used a pressure within the range of 0 to 150 kg/cm$^2$G, preferably 0 to 20 kg/cm$^2$G. Since the object can well be attained without using a particularly high pressure, the pressure level used in the treatment can be suitably decided by taking into account the econimical and other convenience factors.

The amount of diacetoxybutene and diacetoxybutane used in the treatment, though may vary depending on the kind of the discharge gas to be treated, is usually selected from the range of 1 to 1,000 kg/kg of butadiene and acetic acid to be absorbed, preferably 10 to 300 kg/kg of butadiene and acetic acid to be absorbed.

In the step of purifying acetic acid, there arises the necessity of separating acetic acid from water which is a reaction product. Even if they are separated by distillation, a small amount of acetic acid still remains in the water discharged from the top of the distillation tower. It is not only uneconomical but also undesirable from the viewpoint of pollution to release such acetic acid-containing water out of the system. According to this invention, the acetic acid is absorbed by diacetoxybutene and/or diacetoxybutane and can thereby be efficiently recovered and refined.

Any type of apparatus usually used for an absorbing operation may be used for effecting absorption of butadiene and acetic acid in the method of this invention, and such apparatus includes, for example, a packed column, plate column, spray tower, etc.

Diacetoxybutene and diacetoxybutane used as absorbent in this invention need not be purified particularly, and may contain impurities such as water, acetic acid, etc., in such an amount that no inconvenience is caused. Use of a mixture of diacetoxybutene and diacetoxybutane as absorbent is also possible in practicing the method of this invention.

Diacetoxybutene obtained from the acetoxylation reaction of butadiene is a mixture of 1,4-diacetoxybutene-2, which is the principal reaction product, and a small quantity of 3,4-diacetoxybutene-1 which is a by-product. 1,4-Diacetoxybutene-2 only may be separated from said mixture, but in this invention, there is no such necessity and it is advantageous to immediately use the reaction product (diacetoxybutene mixture) for the treatment. Use of diacetoxybutene and/or diacetoxybutane as absorbent is advantageous not only because they have excellent absorbing efficiency for butadiene and acetic acid but also because diacetoxybutene and/or diacetoxybutane which have absorbed butadiene and acetic acid may simply be sent to a distillation tower for separating the reaction product solution composed mainly of butadiene, acetic acid and diacetoxybutene obtained from the reaction of butadiene, acetic acid and oxygen, and there is no need of providing any extra equipments for separation of the absorbent.

The thus obtained absorption solution of diacetoxybutene and/or diacetoxybutane which contains the absorbed butadiene and acetic acid is sent to a distillation tower. The distillation conditions may be suitably selected from a variety of conditions that allow separation of diacetoxybutene and/or diacetoxybutane from the other low-boiling substances, but for the purpose of preventing polymerization of diacetoxybutene, it is desirable to keep the tower bottom temperature at not more than 150° C., and for this purpose, distillation under reduced pressure is recommended. The distillation is preferably performed in the presence of a phenolic compound such as hydroquinone, t-butylcatechol, di-t-butyl-p-cresol, etc., for preventing coloration or polymerization of diacetoxybutene and inhibiting formation of peroxides. Even a better effect is obtained when the distillation is carried out in an atmosphere of an inert gas such as $N_2$ or $CO_2$ in the presence of a phenolic compound. The phenolic compound is usually used in an amount of 1 to 10,000 ppm based on the amount of diacetoxybutene.

Where diacetoxybutene is used as absorbent, the diacetoxybutene is withdrawn from the bottom of the distillation tower while acetic acid, water and butadiene are taken out of the tower top. These three components may be separated, and acetic acid and butadiene may be circulated back to the reaction system. Also, acetic acid may be withdrawn from a middle portion of the distillation tower while taking out butadiene and water from the tower top, and after separation, said two substances, acetic acid and butadiene, may be circulated to the reaction system.

Where diacetoxybutane is used as absorbent, a mixture of diacetoxybutene and diacetoxybutane is withdrawn from the tower bottom and this mixture can be immediately transferred to the hydrogenation step without separation to convert the diacetoxybutene to diacetoxybutane. In this case, it is, of course, possible to recover acetic acid and butadiene and circulate them to the reaction system as in the case of using diacetoxybutene as absorbent.

The hydrogenation of diacetoxybutene can be accomplished by using a catalyst effective for the hydrogenation such as, for example, palladium, nickel, rhodium, etc., under a pressure within the range of atmospheric pressure to 200 kg/cm$^2$G and at a temperature within the range of room temperature to 200° C. The reaction may be easily performed either batchwise or continuously, and no trouble arises even if diacetoxybutane is present in diacetoxybutene.

According to the method of this invention, butadiene and acetic acid in the gas discharge from the absorption apparatus, and diacetoxybutene or diacetoxybutane used as absorbent can be reduced to such a concentration that they cannot be detected by gas chromatography (50 ppm or less).

Therefore, even if said discharge gas is released into the atmosphere with no additional treatment, there is induced no pollution problem.

Figure 2:
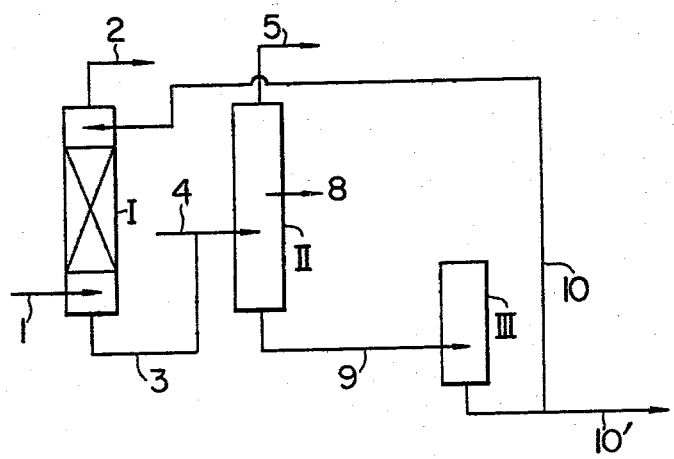
Figure 3:
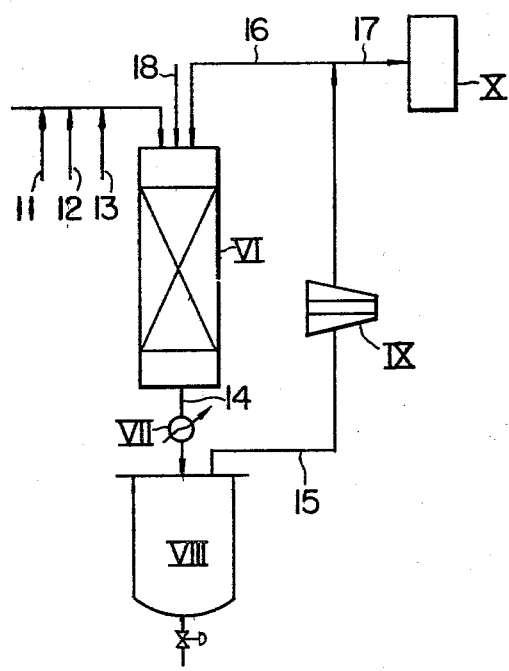

Now, an embodiment of the treating process of this invention is described with reference to the accompanying drawings, in which FIG. 1 is a flow sheet illustrating a process for recovering butadiene and acetic acid, FIG. 2 is a flow sheet illustrating another process for recovering butadiene and acetic acid, and FIG. 3 is a flow sheet showing an acetoxybutene preparation process according to this invention.

Referring first to FIG. 1, I indicates a butadiene and acetic acid absorption tower, and II designates a distillation tower. The butadiene- and acetic acid-containing gas discharged from the reaction system is introduced into the absorption tower I from the conduit 1 while diacetoxybutene is simultaneously supplied into the absorption tower I from the conduit 6 to effect countercurrent contact between said discharge gas and diacetoxybutene. The gas composed mainly of $N_2$ and $O_2$ is discharged from the tower top 2 while diacetoxybutene which has absorbed butadiene and acetic acid is taken out from the tower bottom 3 and guided through a conduit 4 into the distillation tower II together with the reaction product solution. Diacetoxybutene is withdrawn from the bottom of the distillation tower II, and a part of said diacetoxybutene is sent to the absorption tower I through the conduit 6 while the remainder is forwarded to the next step through a conduit 7. The butadiene-water mixture is discharged from the tower top 5 while acetic acid is withdrawn from a side-cut 8. Butadiene and acetic acid are circulated back to the reaction system for reuse.

FIG. 2 is a flow sheet illustrating a process for recovering butadiene and acetic acid by using diacetoxybutane as absorbent. In the drawing, I, II, 1–5 and 8 indicate the same as designated in FIG. 1. III indicates a hydrogenation step for the mixture of diacetoxybutene and diacetoxybutane, 9 a conduit therefor, 10 a conduit for recirculating diacetoxybutane into the absorption tower, and 10' a diacetoxybutane discharge pipe.

In the most preferred embodiment of the process of this invention, the discharge gas from the reaction system is not entirely sent into the absorption tower but only a part of such discharge gas is sent into the absorption tower, with the remaining substantial part thereof being circulated back to the reaction system. Such circulation system is described hereunder.

The unreacted discharge gas formed after separation of the reaction product such as diacetoxybutene produced from the reaction of feed gas composed of butadiene, acetic acid, oxygen and inert gas contains inert gas in excess relative to the amount of unreacted butadiene, so that it is necessary to take out a part of discharge gas for regulating the inert gas quantity. In the preferred circulation system according to this invention, highly concentrated oxygen such as pure oxygen is used as oxygen source, and in this case, the amount of discharge gas to be taken out may be such as given from the following formula:

$$\frac{\text{Amount of } CO_2 \text{ produced in one pass (l./h)}}{\text{Total amount of inert gas passing through catalyst layer (l./h)}} \times 100 \, (\%)$$

and the other discharge gas is circulated back to the reaction system.

Under such conditions, it suffices to treat only a limited portion of the gas discharged from the reaction system, and it is possible to select a high space velocity with no impediment. On the other hand, the amount of butadiene to be supplied into the discharge gas which is circulated for reuse may be merely an amount equivalent to the sum of the amount consumed in the reaction and the amount contained in the withdrawn gas (this portion of butadiene may be recovered in the absorption tower), so that the butadiene reaction rate can be easily elevated to over 90%. There is absolutely no need of freshly supplying an inert gas into the reaction system, and if $CO_2$ is used as the inert gas, a favorable effect is given to the catalyst.

Use of an inert gas is helpful for removing the reaction heat due to dilution of reaction gas, carriage of the reactive gas and diminution of the explosive range, and in this invention, $N_2$, $CO_2$, Ar, He or the like may be suitably used as the inert gas. Among these inert gas substances, $N_2$ and $CO_2$ are preferred because of their inexpensiveness and $CO_2$ is particularly preferred because of the disclosed fact that even if it coexists in large quantities with the reactive gas, it surprisingly causes no catalyst poisoning and rather proves helpful for prolonging the catalyst life.

Thus, the circulation type process of this invention is economically advantageous as the amount of gas to be taken out is limited and hence the butadiene recovery equipments may be on a small scale. Also, since $CO_2$ used as the inert gas is accumulated in the reaction system by the circulation, the catalyst life is amazingly lengthened.

The circulation type process of this invention is described in further detail below with reference to FIG. 3 which illustrates an embodiment of the process using $N_2$ as inert gas.

In FIG. 3, 11, 12 and 13 indicate the conduits of butadiene, $O_2$ and $N_2$, respectively, 18 an acetic acid conduit, VI a reaction vessel, VII a cooling tube, VIII a gas-liquid separator, IX a gas circulator, and X a butadiene absorption apparatus. The reaction materials, butadiene, $O_2$, $N_2$ and acetic acid, are supplied into the reaction vessel VI through their respective conduits 11, 12, 13 and 18 and reacted in the catalyst layer to produce diacetoxybutene. The unreacted gas is cooled in the cooling tube VII and sent to the gas-liquid separator VIII together with diacetoxybutene. In the gas-liquid separator VIII, the mixture of the reaction products, namely diacetoxybutene, $CO_2$ and $H_2O$, and the unreacted butadiene, $O_2$, $N_2$ and acetic acid is subjected to gas-liquid separation. The treatment may be made so that acetic acid is contained in the gaseous components by suitably selecting the separation conditions, but in such case, water is also sent to the catalyst layer together with acetic acid. Water may prove helpful in prolonging the catalyst life, but on the other hand, it may act to reduce the catalyst activity, so that it is essential to determine the gas-liquid separation conditions by giving careful considerations to such factors. Usually, the temperature is selected from within the range of 20° to 150° C. while the pressure is selected from within the range of 0 to 10 kg/cm²G, but these ranges are not critical.

Unreacted butadiene, $O_2$, $N_2$ and $CO_2$, which are the principal constituents of the gaseous phase, are sent to the gas circulator IX through the conduit 15 and then returned to the reaction vessel VI through the conduit 16. A part of the gas is sent to the butadiene absorption apparatus through the conduit 17. After the reaction has reached the steady state, the minimum amount of gas to be taken out (per given time) from the conduit 17 is determined by the following formula:

$$\frac{\text{Amount of } CO_2 \text{ produced (l./h)}}{\text{Amount of } CO_2 \text{ produced} + \text{amount of } N_2 \text{ (l./h)}} \times 100 \, (\%)$$

Although no trouble arises even if the gas is taken out in any greater amount, it is preferred to circulate more than 90% of the discharge gas to the reaction system. The materials that have to be supplied constantly are butadiene, $O_2$ and acetic acid, but as regards butadiene and $O_2$, it suffices to merely supply the quantity equivalent to the sum of the amount consumed in the reaction, the amount contained in the withdrawn gas and the amount absorbed in diacetoxybutene and/or acetic acid in the gas-liquid separator VIII. No fresh supply of $N_2$ is required when the treatment is performed with minimum extraction. The gas circulation may be practiced by using a gas circulation pump, blower or the like.

As for absorption of butadiene in the withdrawn gas, it suffices to treat only a part of the unreacted gas because of use of the gas circulation system, and such absorption treatment can be accomplished more efficiently by using as absorbent the reaction product, diacetoxybutene, or diacetoxybutane obtained by hydrogenation of diacetoxybutene.

Thus, according to the process of this invention, it is possible to efficiently and industrially advantageously recover butadiene and acetic acid from the butadiene and acetic acid-containing discharge gas released in the process for the production of diacetoxybutene from butadiene, acetic acid and oxygen by using a noble metal catalyst such as a palladium catalyst, and also there can be established a closed system which has no possibility of causing any pollution problem.

The process of this invention is now described in further detail by way of some examples thereof, but it will be understood that these examples are intended to be merely illustrative and not restrictive.

EXAMPLE 1

24.1 kg/hr of butadiene, 53.6 kg/hr of acetic acid, 0.6 kg/hr of water and 70 Nm³/hr of nitrogen gas containing 3% by volume of oxygen were supplied contaniously into a packed layer of a silica-alumina catalyst (weight ratio of silica/alumina = 10/90) on which palladium, vanadium, antimony, cesium chloride and potassium acetate were supported, and reacted at 170°–190° C., and 0.2% by volume of the discharge gas from the reaction system was supplied into a butadiene and acetic acid absorption tower while the remainder was circulated to the reaction system. The amount of the discharge gas supplied into the absorption tower was as shown in Table 2, and said discharge gas was treated in the manner described below.

TABLE 2

|  | Discharge gas composition (mol %) | Amount of discharge gas (l./hr) |
|---|---|---|
| Butadiene | 9.8 | 15.7 |
| Acetic acid | 2.8 | 4.5 |
| Water | 0.4 | 0.7 |
| $O_2$ | 1.4 | 2.2 |
| $N_2$ | 85.4 | 136.6 |
| $CO_2$ | 0.1 | 0.2 |

This discharge gas was supplied into an absorption tower with a diameter of 19 mm and a pack height of 1,800 mm (packed with MacMahon filler) and contacted countercurrently with 2.14 kg/hr of diacetoxybutene (97.9% by weight 1,4-structure) separated from the reaction product solution, at an operating temperature of 50° C. at a pressure of 10 kg/cm² abs. After the butadiene and acetic acid had been absorbed by the absorbent (diacetoxybutene), the discharge gas from the tower top (this discharge gas having been composed mainly of $N_2$) was analyzed. The results showed that butadiene, acetic acid and diacetoxybutene (absorbent) were all reduced to such a concentration that they were not detected by gas chromatography.

On the other hand, the diacetoxybutene obtained from the tower bottom (this diacetoxybutene having contained butadiene and acetic acid) was supplied into a distillation tower with an inner diameter of 250 mm and a pack height of 2,300 mm (packed with MacMahon filler) together with the reaction product solution having the composition shown in Table 3, and diacetoxybutene and other low-boiling substances were separated by an operation conducted under the following conditions: tower bottom temperature of 150° C., tower top temperature of 52° C. and pressure of 0.08 kg/cm² abs. There was thus obtained 14.1 kg/hr of diacetoxybutene, 15% by weight of which was supplied into the absorption tower for use as absorbent and the remainder was sent to the next step.

TABLE 3

| Reaction product solution | Composition (wt %) |
|---|---|
| Butadiene | 2.9 |
| Acetic acid | 72.2 |
| Water | 2.9 |
| 3,4-Diacetoxybutene | 0.4 |
| 1,4-Diacetoxybutene | 21.6 |

EXAMPLE 2

After performing the reaction in completely the same way as in Example 1, 0.2% by volume of the discharge gas was supplied into the same absorption tower as in Example 1 and contacted countercurrently with 1.80 kg/hr of diacetoxybutane at an operating temperature of 50° C. at a pressure of 10 kg/cm² abs. After the butadiene and acetic acid had been absorbed by the diacetoxybutane, the discharge gas from the absorption tower top, composed mainly of $N_2$, was analyzed by gas chromatography, which showed that the butadiene, acetic acid and diacetoxybutane concentrations were all below the limit of detection.

On the other hand, the diacetoxybutane (containing butadiene and acetic acid) obtained from the tower bottom was supplied into the distillation tower of Example 1 together with the same reaction product solution as used in Example 1 and subjected to a separation operation at a tower bottom temperature of 155° C., a tower top temperature of 52° C. and a pressure of 0.08 kg/cm² abs. to separate the mixture of diacetoxybutene and diacetoxybutane from the other low-boiling substances. The obtained mixture of diacetoxybutene and diacetoxybutane at a weight ratio of 6.8:1 was sent to the hydrogenation step without separation and reached in the presence of 5% by weight of Pd-carbon catalyst (made by Engelhardt) at a hydrogen pressure of 10 kg/cm²G at a temperature of 50° C. for three hours. As a result, 99.9% by weight of diacetoxybutene was converted into diacetoxybutane, and the latter was obtained at a rate of 14.1 kg/hr, 12.8% by weight of which was supplied to the absorption tower as an absorbent for the butadiene and acetic acid.

EXAMPLE 3

One liter of a silica-alumina catalyst (weight ratio of silica/alumina=10/90) on which palladium, vanadium, antimony, cesium chloride and potassium acetate were supported was packed in a stainless steel reaction vessel with an inner diameter of 1.5 inches, and butadiene, acetic acid, oxygen and nitrogen were supplied so that they might pass through the catalyst layer at rates of 100 l./hr, 200 l./hr, 30 l./hr and 670 l./hr, respectively, and reacted at 170°–190° C. therein. As a result, diacetoxybutene was obtained at a space time yield of 0.75 mol/l.cat·hr and $CO_2$ at a space time yield of 0.048 mol/l.cat·hr. The reaction product containing these substances was subjected to gas-liquid separation under the conditions of 40° C. and 0.5 kg/cm²G, and 99.8% by volume of the gaseous component was circulated back to the reaction system. This means that the amount of butadiene to be taken out, that is, the amount of butadiene treated, was only 0.2% by volume of the gaseous component. The butadiene and oxygen supplies in the steady state were 23.5 l./hr and 9.9 l./hr, respectively, and not supply of nitrogen was required. The amount of the carbon dioxide gas in the system reached 80.2% by volume of the inert gas in the steady state. As a result, diacetoxybutene was obtained at a space time yield of 0.68 mol/l.cat·hr on the 70th day after the start of the reaction, and little drop of activity was seen.

EXAMPLE 4

The reaction was carried out in the same way as in Example 1, except that carbon dioxide gas was substituted for the nitrogen, and as a result diacetoxybutene was obtained at a space time yield of 0.77 mol/l.cat·hr and $CO_2$ at a space time yield of 0.045 mol/l.cat·hr. The reaction product was subjected to gas-liquid separation in the same manner as in Example 1, and only 0.15% by volume of the gaseous component (which was the amount equivalent to the amount of carbon dioxide gas produced) was taken out of the circulation system. The butadiene and oxygen feeds in the steady state were 23.8 l./hr and 10.0 l./hr, respectively, and no fresh supply of $CO_2$ was needed. On the 70th day after the start of the reaction, diacetoxybutene was obtained at a space time yield of 0.74 mol/l.cat·hr, and substantially no drop of activity took place.

EXAMPLE 5

Butadiene, acetic acid, air and $N_2$ were passed at rates of 100 l./hr, 200 l./hr, 150 l./hr and 550 l./hr, respectively, by using the same catalyst as in Example 1. That is, the reaction was performed under the same conditions as in Example 1, except that air is oxygen source was used. As a result, diacetoxybutene was obtained at a space time yield of 0.73 mol/l.cat·hr and $CO_2$ at a space time yield of 0.049 mol/l.cat·hr.

The reaction product was subjected to gas-liquid separation under the same conditions as in Example 1, and 93.1% by volume of the gaseous component was circulated back to the reaction system. Even when air was used as oxygen source, the required amount of the matter taken out from the reaction system was as low as only 6.9% by volume. The butadiene and air feeds in the steady state were 28.7 l./hr and 56 l./hr, respectively, and no supply of nitrogen was necessitated. The amount of the carbon dioxide gas in the system reached 2.6% by volume of the inert gas in the steady state. The space time yield of the diacetoxybutene on the 70th day was 0.64 mol/l.cat·hr.

What is claimed is:

1. In a process for the production of diacetoxybutene wherein butadiene, acetic acid and oxygen are reacted in the presence of a catalyst and an inert gas to produce said diacetoxybutene and a discharge gas composed mainly of butadiene, acetic acid, oxygen and an inert gas released from the reaction, the improvement comprising separating said discharge gas into a first portion which is circulated back to the reaction for reuse and a second portion which is supplied to an absorption tower wherein said second portion is contacted with diacetoxybutene, diacetoxybutane or a mixture thereof.

2. The process according to claim 1, wherein said first portion of said discharge gas comprises more than 90% by volume of said discharge gas.

3. The process according to claim 1, wherein the amount of discharge gas to be taken out as said second portion for feed into the absorption tower is:

$$\frac{\text{Amount of } CO_2 \text{ produced in one pass (l./h)}}{\text{Total amount of inert gas passing through catalyst (l./h)}} \times 100\%.$$

4. The process according to claim 1, wherein $CO_2$ is used as the inert gas.

* * * * *